United States Patent [19]
Kaufman

[11] Patent Number: 6,042,287
[45] Date of Patent: Mar. 28, 2000

[54] SURGICAL SCRUB BRUSH-SPONGE

[76] Inventor: Jack W. Kaufman, 357 Frankel Blvd., Merritt, N.Y. 11566

[21] Appl. No.: 09/241,122

[22] Filed: Feb. 1, 1999

[51] Int. Cl.$^7$ ...................................................... A47L 1/08
[52] U.S. Cl. .............................. 401/24; 401/39; 401/14; 15/114
[58] Field of Search .................... 401/6, 23, 24, 401/39, 8, 14; 15/114, 107, 106, 244.4, 244.1

[56] References Cited

U.S. PATENT DOCUMENTS

| | | | |
|---|---|---|---|
| D. 287,430 | 12/1986 | Kaufman . | |
| 624,055 | 5/1899 | Lawrence | 401/14 |
| 3,447,181 | 6/1969 | Coker et al. | 15/114 |
| 3,467,978 | 9/1969 | Golden | 15/114 |
| 3,707,012 | 12/1972 | Lane | 15/104.93 |
| 4,111,666 | 9/1978 | Kalbow | 51/295 |
| 4,407,213 | 10/1983 | Evans | 14/222 |
| 4,420,853 | 12/1983 | Gilman . | |
| 4,903,365 | 2/1990 | Kaufman | 15/110 |
| 5,312,197 | 5/1994 | Abramson | 401/6 |

Primary Examiner—Henry J. Reca
Assistant Examiner—Huyen Le
Attorney, Agent, or Firm—David Fink

[57] ABSTRACT

A surgical scrub brush-sponge has an extension in providing additional surface area for cleansing and retaining solvents and solutions used during the cleansing process. Where a portion of the sponge-like element of the brush extends beyond the base of the brush and conforms to an end of the base. Additionally, the portion may be made to extend beyond the base covering the brush bristles on that end of the brush-sponge.

2 Claims, 6 Drawing Sheets

SURGICAL SCRUB BRUSH-SPONGE

TECHNICAL FIELD

The present invention relates to a surgical scrub brush-sponge extension which provides additional surface area for cleansing and retaining solvents and solution used during the cleansing process.

BACKGROUND OF THE INVENTION

Scrub brushes are used in many applications when greater cleansing is required or desired, as when medical professionals prepare for surgery. The surgical scrub brush is made of a durable material, such as plastic, and extending from this plastic base are rows of bristles creating a brush-like form. This brush-like form is used for deep cleansing and scrubbing of hands, fingers, nails and knuckles. Attached to the scrub brush is a sponge-like material, where the sponge-like material retains solution and solvents and transports the solvents to the cleansing surface. The brush and sponge are usually attached one on top of the other, leaving exposed the hard edges of the base at the point the two materials join. These hard edges provide zones where an injury to the hands, fingers, nails or knuckles of one using the scrub brush, can occur.

SUMMARY OF THE INVENTION

The present invention overcomes the disadvantages of causing an injury by providing a covering over the exposed surfaces of the hard base material. The covering of the hard edges is obtained by extending the softer sponge-like material beyond the base unit and folding this extended sponge-like material over the hard boundary edges of the base unit.

As used herein, the term sponge-like material refers to materials which are typical of materials used to retain solvents held in solution and used in applying the solvents during cleansing of, for example, hands, fingers, nails and knuckles.

For a fuller understanding of the nature and objects of the invention, reference should be had to the following detailed description, taken in connection with the accompanying drawings.

DETAILED DESCRIPTION OF THE DRAWINGS

DETAILED DESCRIPTION OF THE PREFERRED EMBODIMENTS

Figure 1:
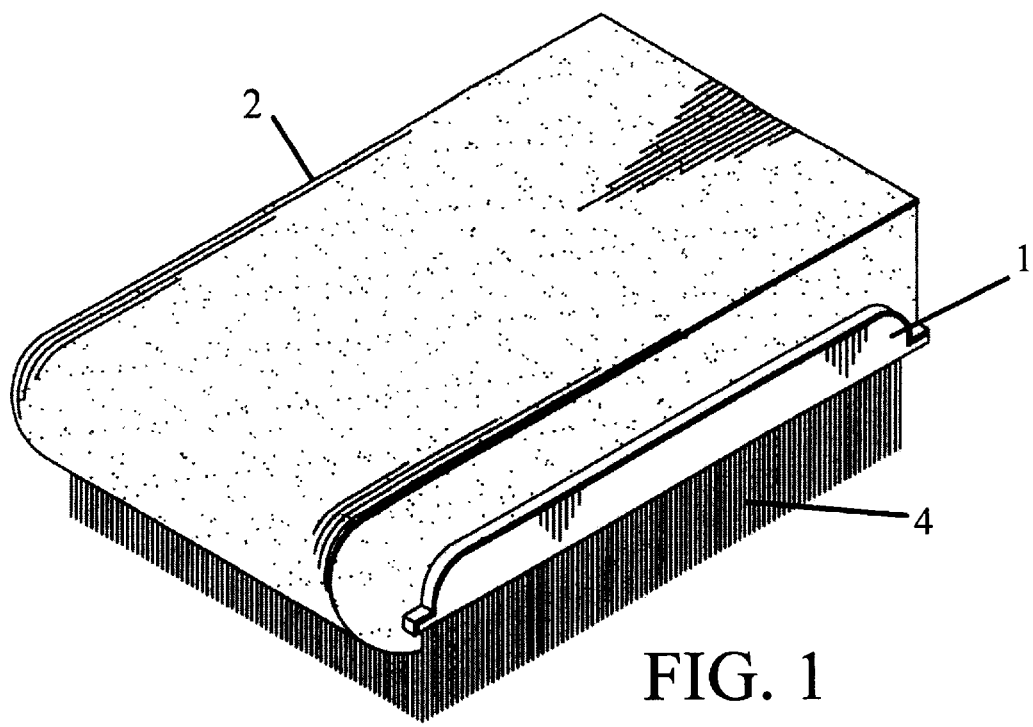
FIG. 1 is a perspective view of one embodiment according to the invention.
Figure 2:
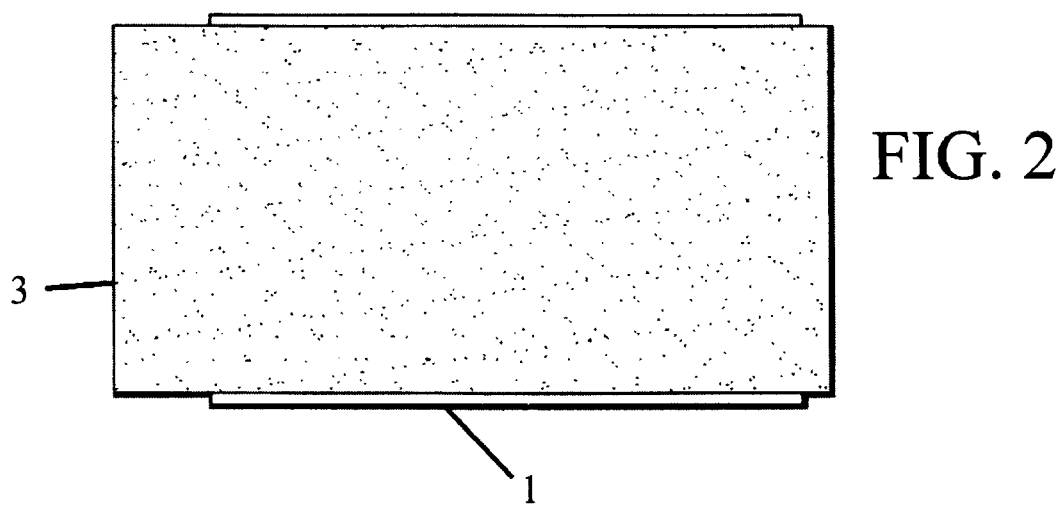
FIG. 2 is a top view of the embodiment shown in FIG. 1.
Figure 3:
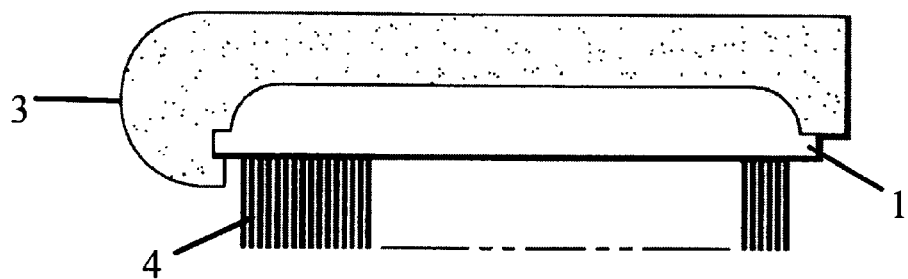
FIG. 3 is a side elevational view of the embodiment shown in FIG. 1.
Figure 4:
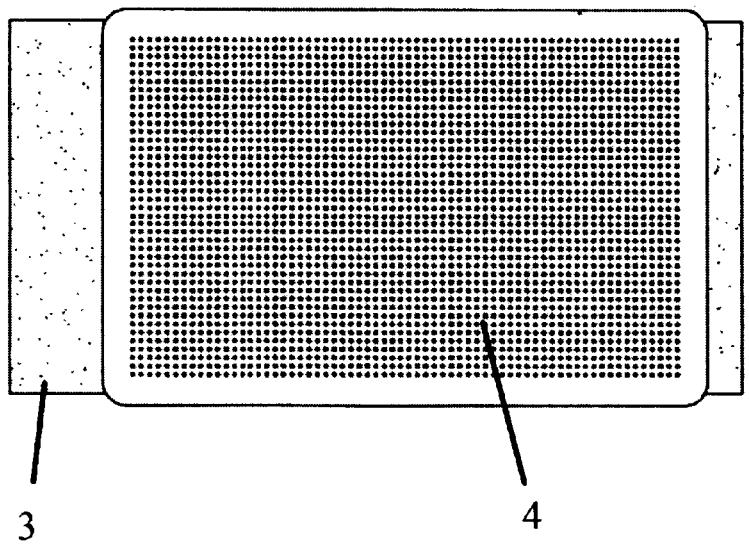
FIG. 4 is a bottom view typical of a brush-like pattern of the embodiment shown in FIG. 1.
Figure 5:
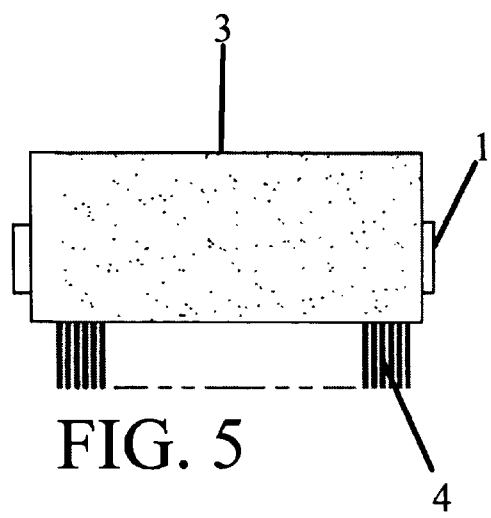
FIG. 5 is an elevational view of one end of the embodiment shown in FIG. 1.
Figure 6:
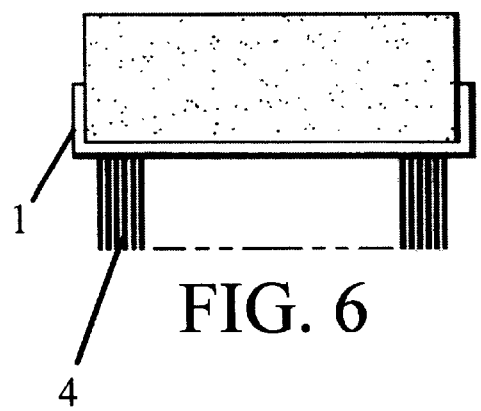
FIG. 6 is an elevational view of the end of the embodiment shown in FIG. 1 opposite the end shown in FIG. 5.

FIG. 1 shows a perspective view of a preferred embodiment of the surgical scrub-brush according to the invention. FIG. 3 shows a side elevational view and FIGS. 5 and 6 show an elevational view of each end of the scrub brush shown in FIG. 1. The base element 1 is shown with bristle-like elements 4 extending downward, forming a stable foundation. FIG. 1 further shows a sponge-like material attached to the base element. A portion 3 of the sponge-like material 2 is shown extending beyond the plastic base element and covering conformingly to an end surface of the plastic base element 1, leaving the bristle-like elements 4 exposed. FIG. 5 illustrates how the portion 3 leaves the end elements exposed.

Figure 7:
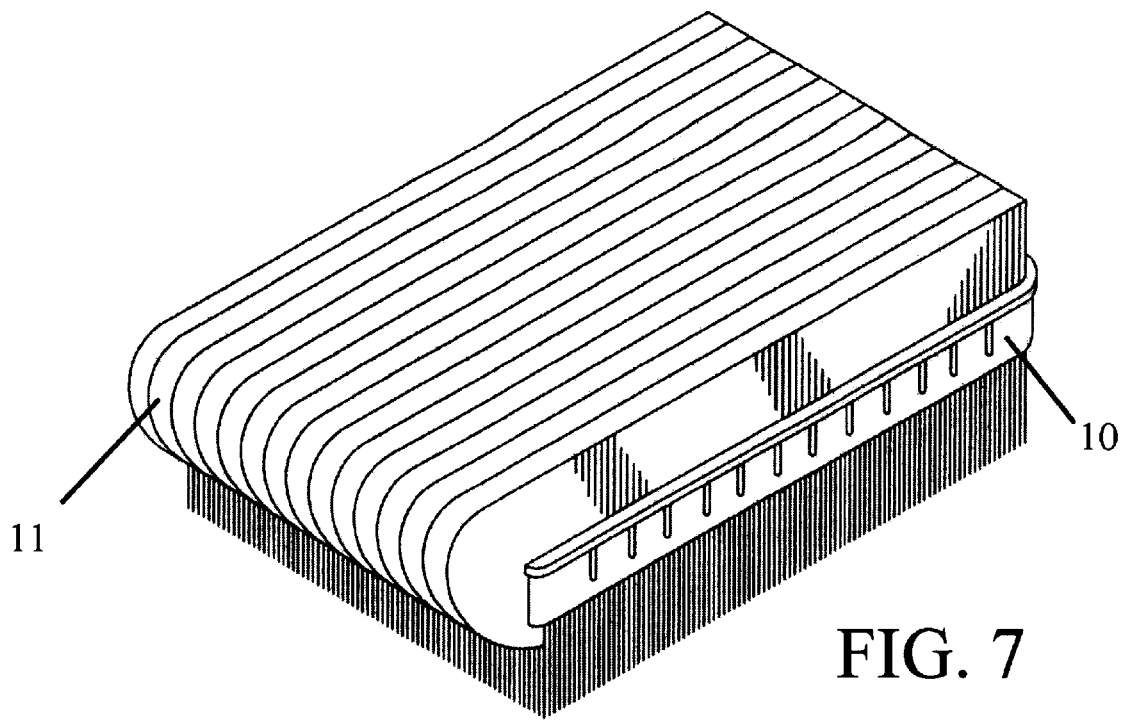
FIG. 7 is a perspective view of another embodiment according to the invention.
Figure 8:
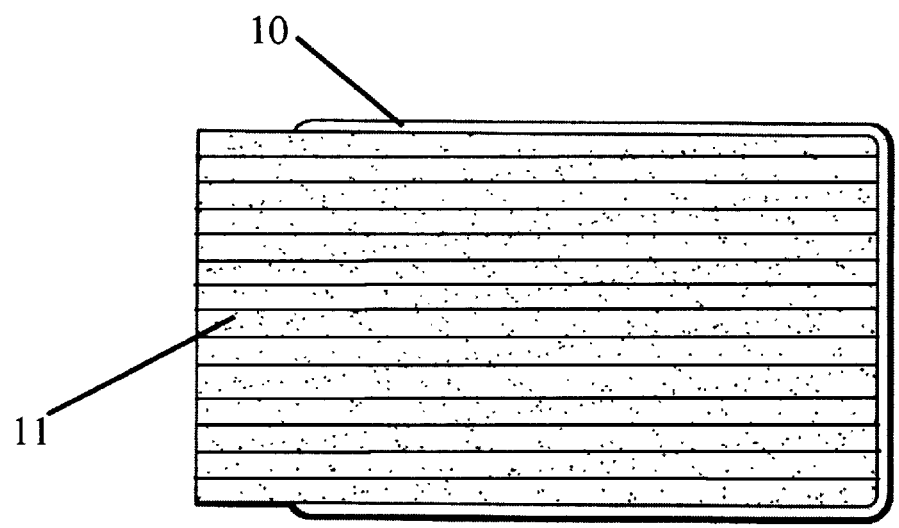
FIG. 8 is a top view of the embodiment shown in FIG. 7.
Figure 9:
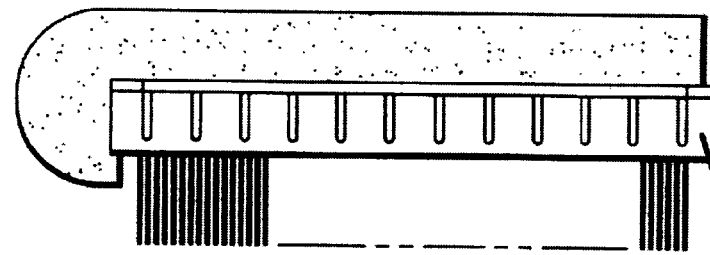
FIG. 9 is a side elevational view of the embodiment shown in FIG. 7.
Figure 10:
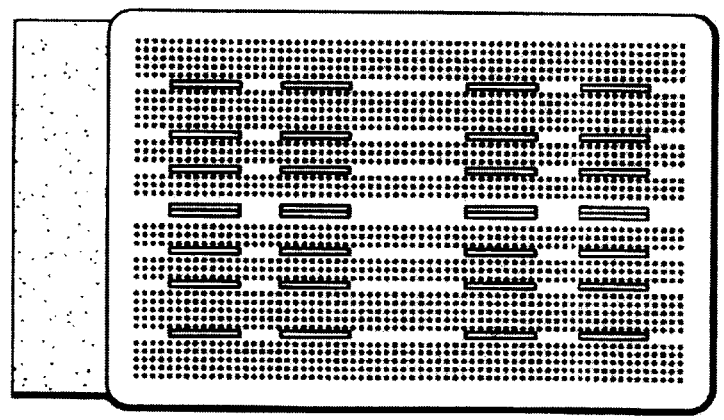
FIG. 10 is a bottom view typical of a brush-like pattern of the embodiment shown in FIG.7.
Figure 11:
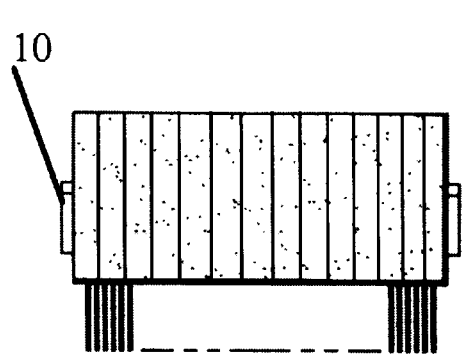
FIG. 11 is an elevational view of one end of the embodiment shown in FIG. 7.
Figure 12:
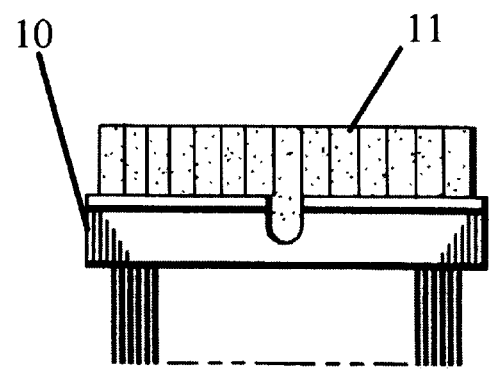
FIG. 12 is an elevational view of the end of the embodiment shown in FIG. 7 opposite the end shown in FIG. 11.

FIG. 7 shows another embodiment of the brush-sponge according to the invention. FIG. 8 shows a top view of the sponge-like material with a horizontal grooved pattern 11 with respect to the front edge of the base element 10. This horizontal pattern and the number of grooves depicted are examples of the pattern that can be scored into the sponge-like material, and is not the only pattern considered. The grooving of the sponge-like material provides additional surface area for cleansing and retaining solvents used in the cleansing process. In this embodiment the sponge-like material covers the end hard edge as shown in FIG. 9. However, horizontal grooved pattern 11 could also be used in the embodiments shown in FIGS. 1 and 13.

Figure 13:
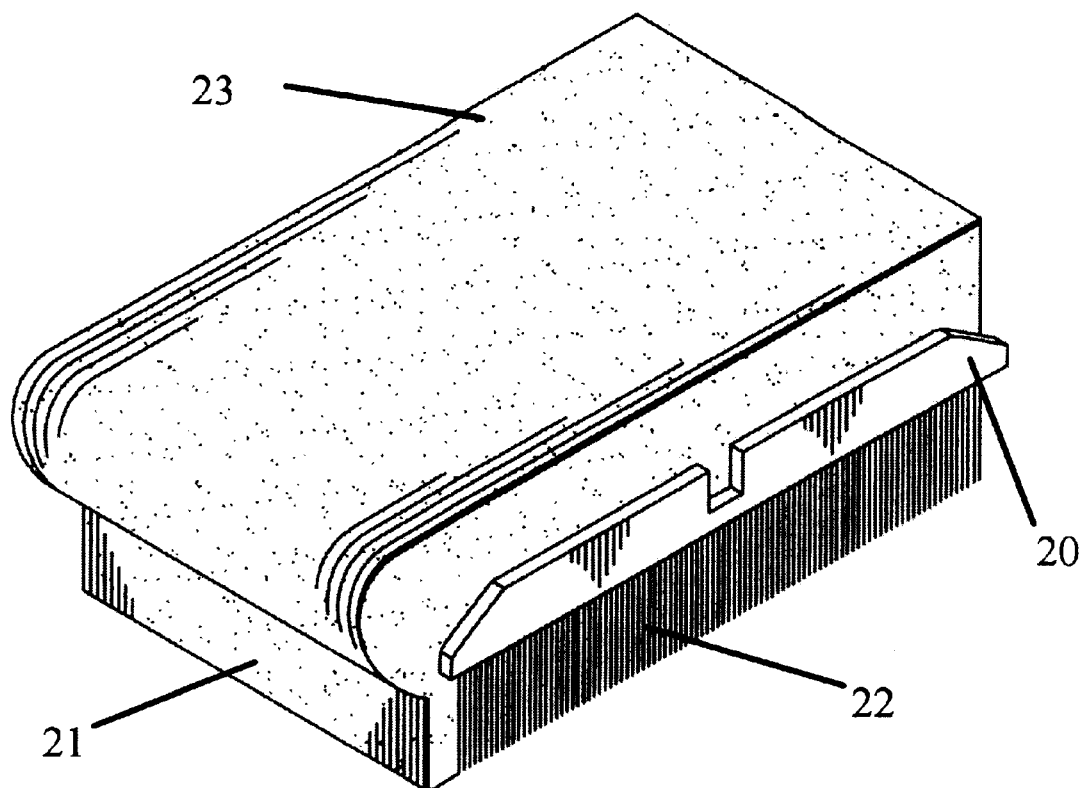
FIG. 13 is a perspective view of yet another embodiment according to the invention.
Figure 14:
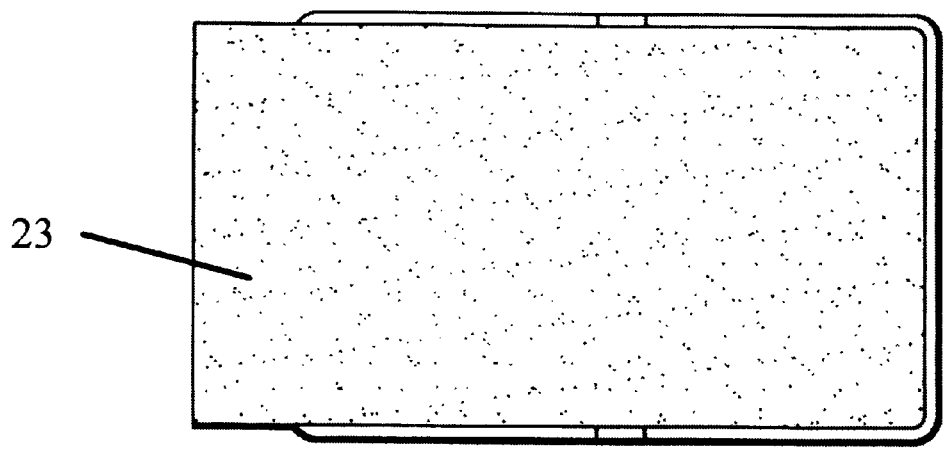
FIG. 14 is a top view of the embodiment shown in FIG. 13.
Figure 15:
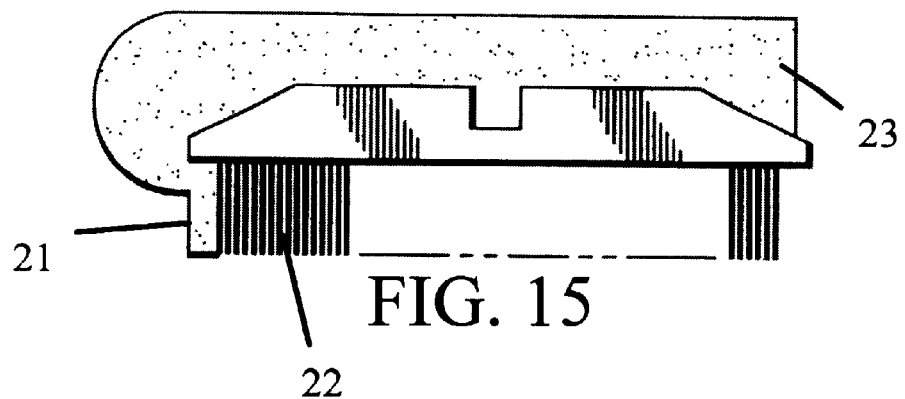
FIG. 15 is a side elevational view of the embodiment shown in FIG. 13.
Figure 16:
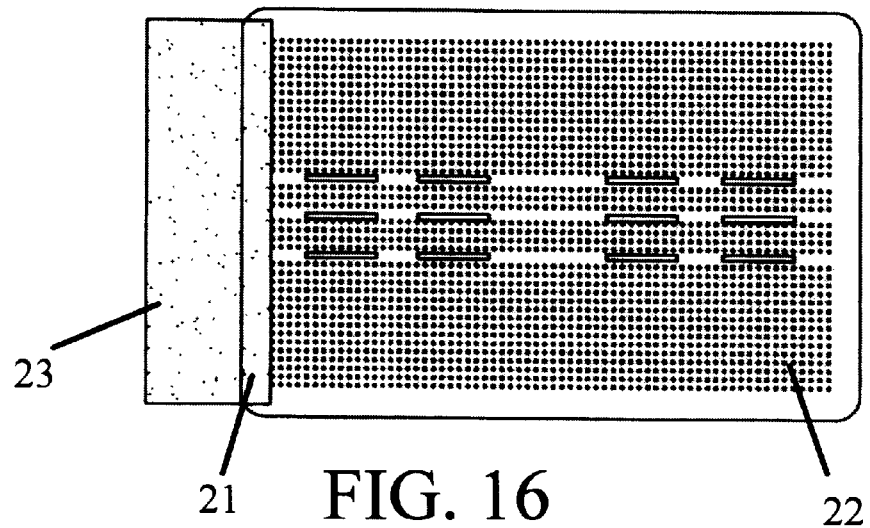
FIG. 16 is a bottom view typical of a brush-like pattern of the embodiment shown in FIG. 13.
Figure 17:
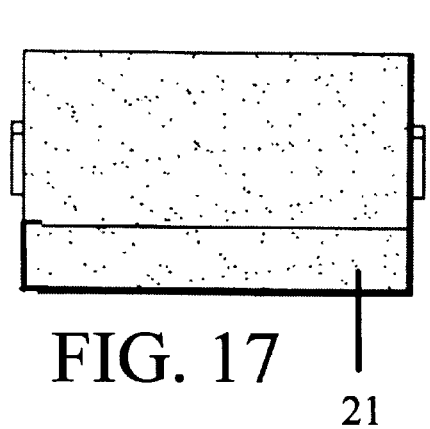
FIG. 17 is an elevational view of one end of the embodiment shown in FIG. 13.
Figure 18:
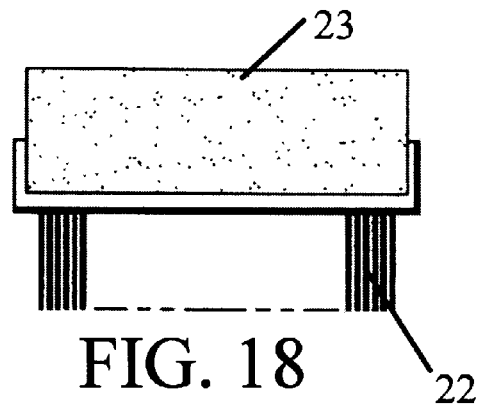
FIG. 18 is an elevational view of the end of the embodiment shown in FIG. 13 opposite the end shown in FIG. 17.

FIG. 13 shows yet another embodiment of the brush-sponge according to the invention. FIG. 13 shows a base element 20 with bristle-like elements 22 and a sponge-like material 23. A portion 21 of material 23 extends beyond base element 20 and covering an end surface of base element 20. Portion 21 extends further to cover the bristle-like elements the end of the brush. This complete covering provides maximum protection from the hard edge of the base element, as in the embodiments shown in FIGS. 1 and 7, and also be protected unintentionally encountering the end bristle-like elements.

The advantage of this configuration enables one using the sponge-like edge on the front edge without risking injury to the hand, finger, nail or knuckle being scrubbed.

There has been described a novel sponge-like extension to a surgical scrub-brush. It is evident that those skilled in the art may now make numerous uses and modifications of and departures from the specific embodiments described herein without departing from the inventive concepts. Consequently, the invention is to be construed as embracing each and every feature and novel combination of features present or possessed by the accessory herein disclosed and limited solely by the spirit and scope of the appended claims.

What is claimed is:

1. An improved surgical scrub brush-sponge, adapted to prevent injuries encountered from scraping against a hard edge and to provide additional cleansing surface area comprising;

a base element having an upper surface and a lower surface; said lower surface having a plurality of bristles, each having a lower end forming a brush-like surface; said brush-like surface used for scrubbing and deep cleaning; said upper surface having walls extending upwardly along the edges of said base element;

an upper cleansing material, a portion including or comprising a sponge-like material, attached to said upper surface of said base element; said upper cleansing material retaining solutions and solvents used in the scrubbing process; said upper cleansing material extending beyond at least one edge of said base element; said extended upper cleansing material conforming to said at least one edge and being attached to said base element; said conforming edge providing protection from scraping against said at least one edge of said base element; wherein said extended upper cleansing material being aligned with said lower ends of said bristles providing additional surface area for protection from injury and cleansing.

2. The surgical scrub brush-sponge as claimed in claim 1; wherein said upper cleansing material contains a plurality of grooves formed by scoring said upper cleansing material; said scored grooves providing additional surface area for cleansing and scrubbing.

* * * * *